US010646332B2

(12) United States Patent
Halpin et al.

(10) Patent No.: US 10,646,332 B2
(45) Date of Patent: May 12, 2020

(54) ADJUSTABLE BASEPLATE FOR USE WITH IRREGULAR TRACHEOSTOMAS

(71) Applicant: Freudenberg Medical, LLC, Carpinteria, CA (US)

(72) Inventors: Michelle Halpin, Santa Barbara, CA (US); John C. Day, Goleta, CA (US); Alex Shen, Berkeley, CA (US); Dimitri Stroumpoulis, Santa Barbara, CA (US)

(73) Assignee: Freudenberg Medical, LLC, Carpinteria, CA (US)

( * ) Notice: Subject to any disclaimer, the term of this patent is extended or adjusted under 35 U.S.C. 154(b) by 85 days.

(21) Appl. No.: 15/824,594

(22) Filed: Nov. 28, 2017

(65) Prior Publication Data

US 2019/0159892 A1 May 30, 2019

(51) Int. Cl.
*A61F 2/20* (2006.01)
*A61M 16/04* (2006.01)
*A61F 13/12* (2006.01)
*A61M 16/10* (2006.01)

(52) U.S. Cl.
CPC ............ *A61F 2/20* (2013.01); *A61F 13/128* (2013.01); *A61M 16/047* (2013.01); *A61M 16/0468* (2013.01); *A61M 16/1045* (2013.01); *A61M 2209/088* (2013.01)

(58) Field of Classification Search
CPC ............ A61M 16/0465; A61M 16/04; A61M 16/0434; A61M 16/047; A61M 16/0468; A61M 16/1045; A61M 2209/088; A61F 2/20; A61F 13/128
See application file for complete search history.

(56) References Cited

U.S. PATENT DOCUMENTS

| 7,025,784 B1 | 4/2006 | Blom et al. |
| D847,982 S | 5/2019 | Falkenberg |
| 2004/0204759 A1* | 10/2004 | Blom ............... A61F 2/203 623/9 |
| 2011/0247629 A1* | 10/2011 | Persson ............ A61M 16/047 128/207.14 |

FOREIGN PATENT DOCUMENTS

| EP | 0 078 685 A1 | 5/1983 |
| EP | 3 153 201 A2 | 4/2017 |

(Continued)

OTHER PUBLICATIONS

European Search Report dated Feb. 5, 2019 (corresponding to EP 18185657.6).

*Primary Examiner* — Brian A Dukert
*Assistant Examiner* — Rebecca Lynee Zimmerman
(74) *Attorney, Agent, or Firm* — Daniel J. Sepanik, Esq.; Harness, Dickey & Pierce, P.L.C.

(57) ABSTRACT

An adjustable base plate for use with a tracheotomy stoma includes a flexible membrane and a base component having an accessory mounting portion disposed in a center of the flexible membrane and adapted to mount a tracheostoma accessory. The base plate defines a conically shaped region formed by a plurality of conforming members extending radially from the accessory mounting portion that are laterally spaced from one another and connected to one another by a plurality of web portions formed by the flexible membrane. An adhesive material is applied to the flexible membrane.

14 Claims, 4 Drawing Sheets

(56) References Cited

FOREIGN PATENT DOCUMENTS

| EP | 3 153 202 A2 | 4/2017 | |
|----|----|----|----|
| GB | 2 517 680 A | 3/2015 | |
| WO | 2004/000401 A1 | 12/2003 | |
| WO | WO-2004000401 A1 * | 12/2003 | .......... A61M 16/047 |
| WO | 2010/070087 A2 | 6/2010 | |
| WO | 2014/090549 A1 | 6/2014 | |

* cited by examiner

ADJUSTABLE BASEPLATE FOR USE WITH IRREGULAR TRACHEOSTOMAS

FIELD

The present disclosure relates to an adjustable base plate for mounting a tracheostoma accessory, such as, but not limited to, a heat and moisture exchanger (HME), a valve, a hands free valve or a shower guard to an irregular tracheostoma.

BACKGROUND

This section provides background information related to the present disclosure which is not necessarily prior art.

Numerous tracheostoma accessories can be used by a patient after a tracheotomy. The accessories can include a heat and moisture exchanger (HME), a valve, a hands free valve or a shower guard, as well as other accessories. A base plate has been known for mounting the accessories to the tracheostoma. The base plate generally includes a mounting portion in the form of a cylindrical sleeve and a flexible skirt that can be adhered to the patient's neck, around the tracheostoma.

SUMMARY

This section provides a general summary of the disclosure, and is not a comprehensive disclosure of its full scope or all of its features.

It is desirable to provide a base plate that is adjustable for use with irregular tracheostomas. In particular, in some patients, the neck region surrounding the tracheostoma is not flat or is irregular so that a flat skirt of a conventional base plate does not adhere well around the tracheostoma.

Accordingly, the present application is directed to an adjustable base plate for use with a tracheotomy stoma including a flexible, elastic membrane and a base component bonded to the flexible membrane and including an accessory mounting portion disposed in a center of the flexible membrane and adapted to mount a tracheostoma accessory, a plurality of conforming members extend radially outward from and are angled relative to the accessory mounting portion and are bonded to the flexible membrane to define a conically shaped region with the conforming members laterally spaced from one another; and an adhesive material applied to the flexible membrane.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
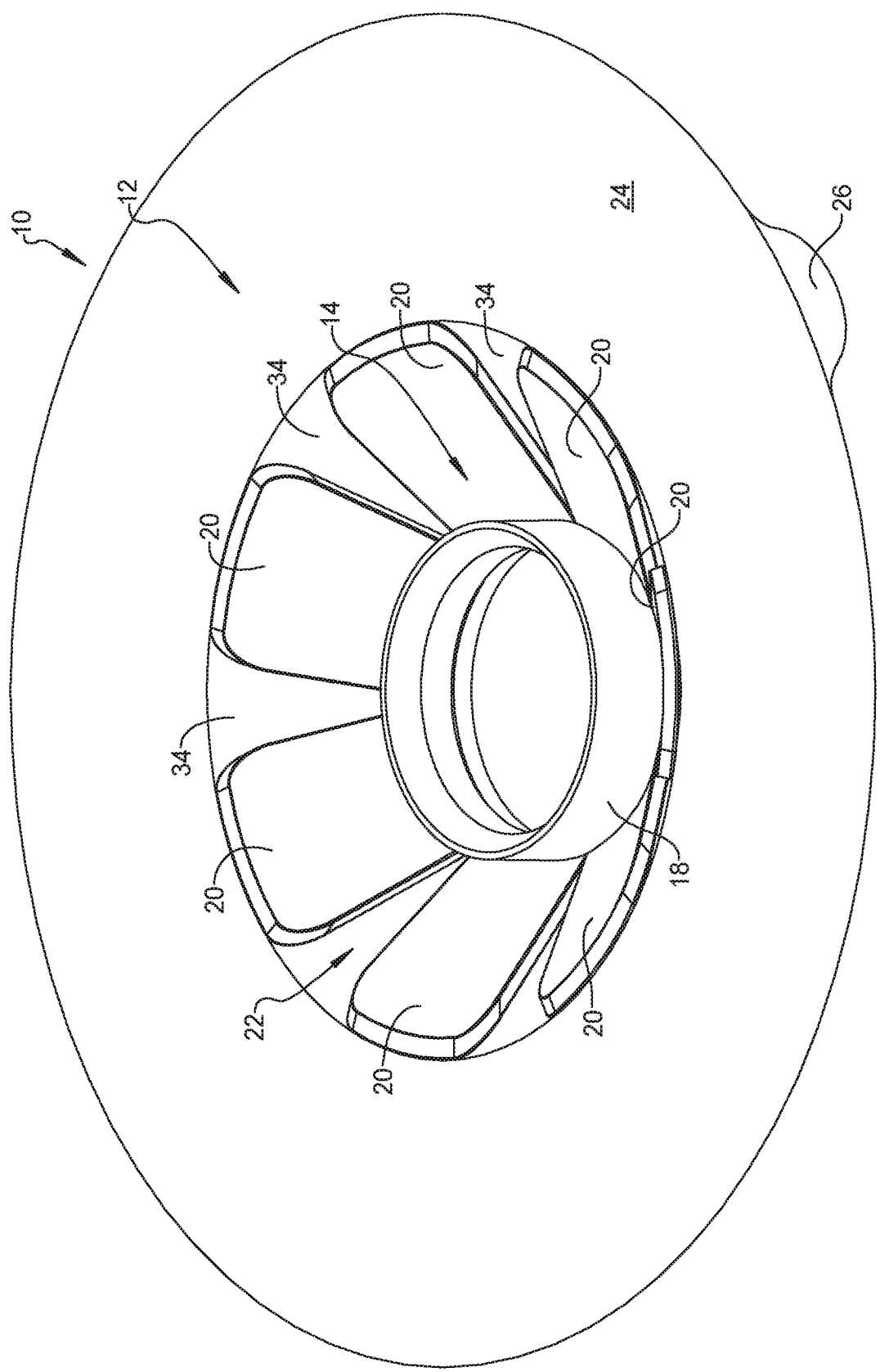
FIG. 1 is a perspective view of an adjustable base plate according to the principles of the present disclosure.
Figure 2:
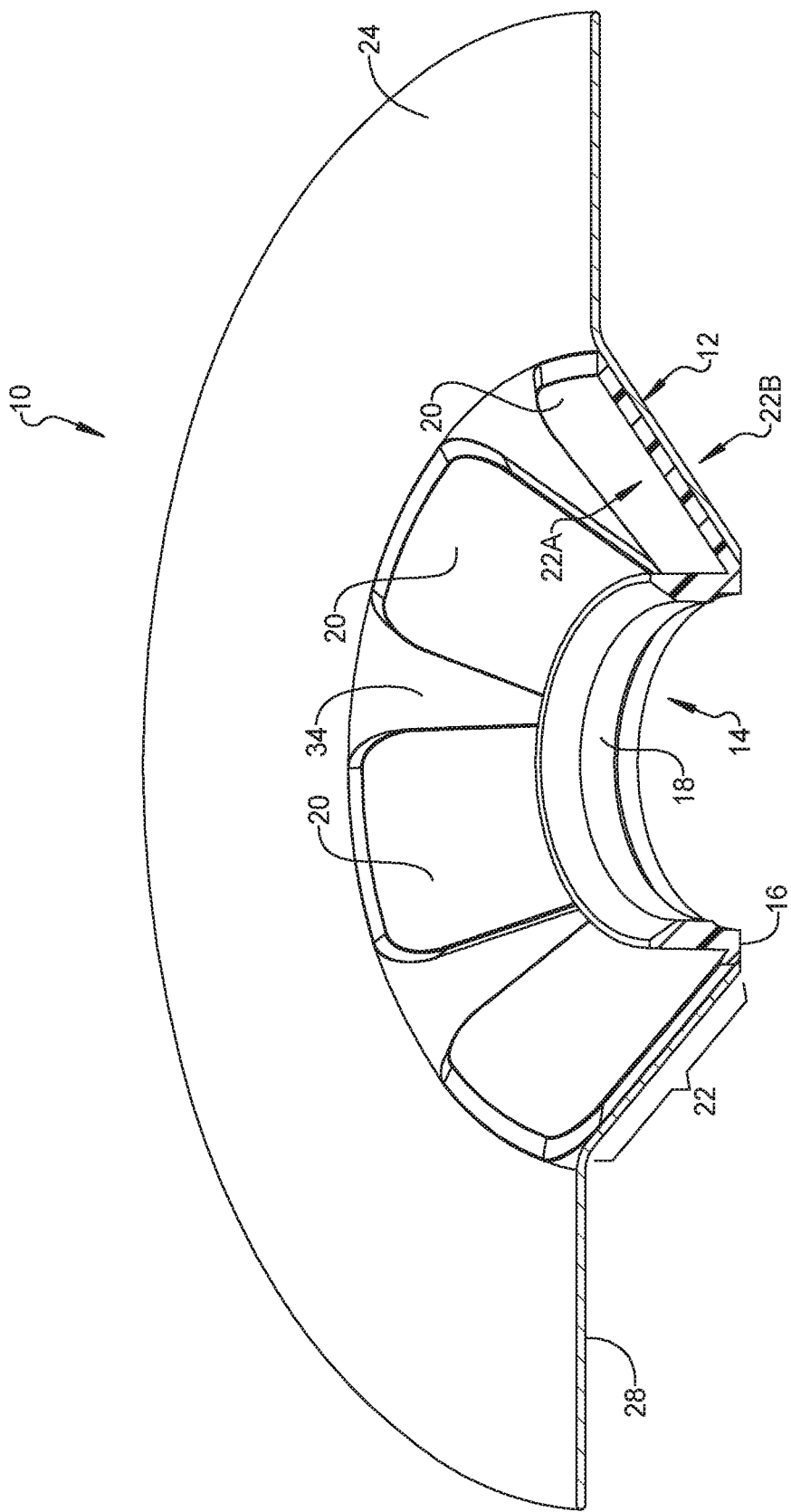
FIG. 2 is a cross-sectional perspective view of the adjustable base plate shown in FIG. 1 of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, heat and moisture exchange component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With reference to FIG. 1, an adjustable base plate 10 for use with a tracheotomy stoma will now be described. The adjustable base plate 10 includes a flexible membrane 12 and a base component 14 bonded to the flexible membrane 12. The base component 14 and the flexible membrane 12 can be bonded together by a laser weld, heat weld, RF weld, or by the use of an adhesive, or other known bonding techniques. The flexible membrane 12 can be made from a polyurethane film or other similar material and can be formed as a flat disk with an opening 16 in a center.

Figure 3:
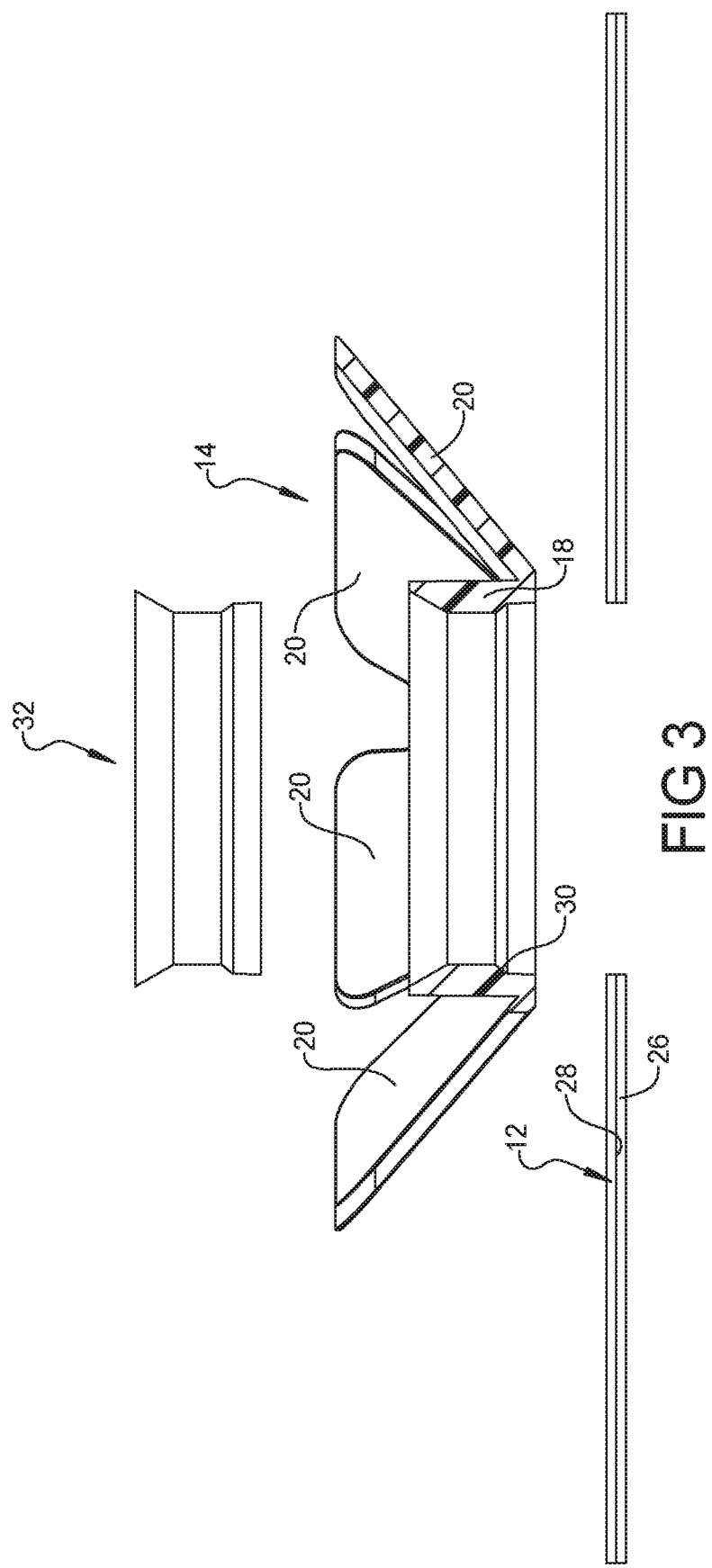
FIG. 3 is a cross-sectional view of the base component of the adjustable base plate shown in FIG. 1 of the present disclosure.
Figure 4:
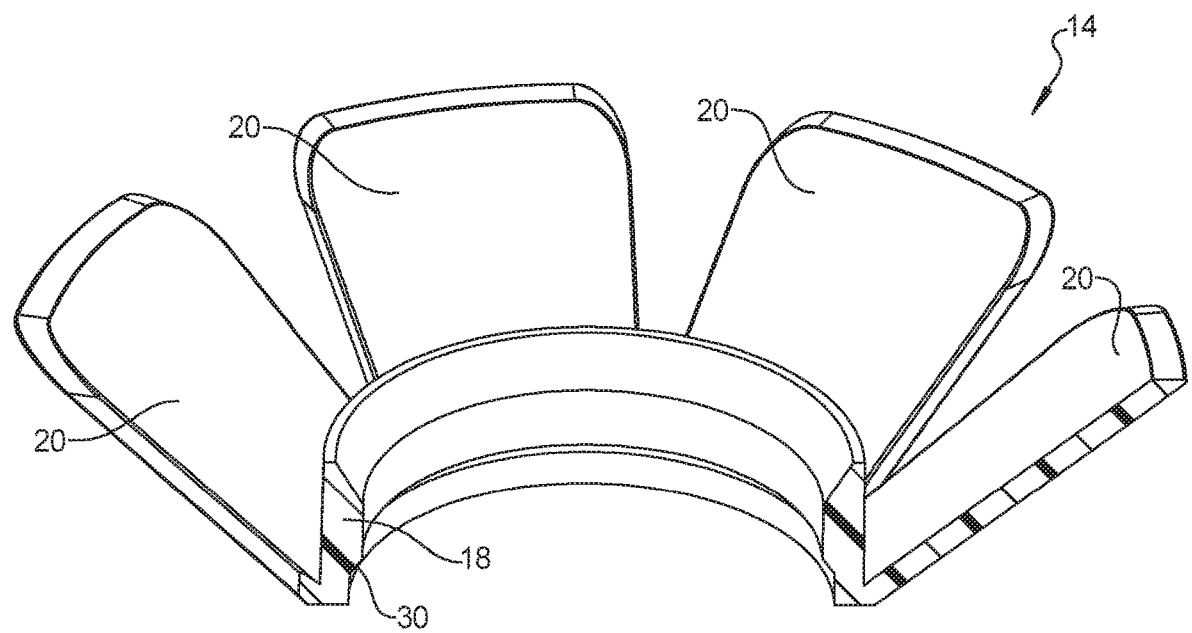
FIG. 4 is a cross-sectional top perspective view of the base component of the adjustable base plate shown in FIG. 1 of the present disclosure.
Figure 5:
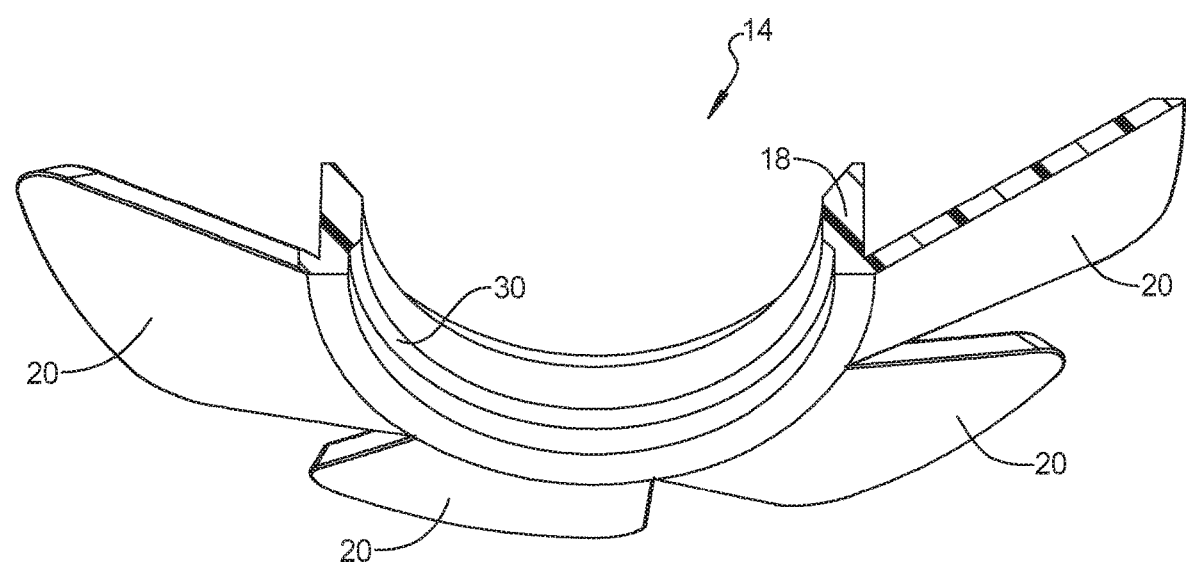
FIG. 5 is a cross-sectional bottom perspective view of the base component of the adjustable base plate shown in FIG. 1 of the present disclosure.

The base component 14 (best shown in cross-section in FIGS. 3-5) includes a generally cylindrical accessory mounting portion 18 and a plurality of conforming members 20 extending radially outwardly from the accessory mounting portion 18. The plurality of conforming members 20 are angled relative to the accessory mounting portion 18 so as to combine with the flexible membrane 12 to form a central conical region 22 of the adjustable base plate 10 surrounding the accessory mounting portion 18. The conforming members 20 are angled so as to provide better retention in the tracheostoma and resist outward forces exerted during use with tracheostoma accessories. The flexible membrane 12 further defines a generally planar region 24 that extends radially outward from the central conical region 22. The generally planar region 24 and the central conical region 22 can be coated with an adhesive material 28. A release liner 26 (shown partially peeled away in FIG. 1) can be adhered to the flexible membrane 12 to cover the adhesive material 28 during handling and can be removed to expose the adhesive material 28 prior to application to a tracheostoma.

The base component 14 can be made from a polyurethane or other similar material and preferably have a more rigid construction than the flexible membrane 12. The accessory mounting portion 18 can include a retention shoulder 30 that can retain an accessory 32 in connection with the accessory mounting portion 18. The accessories can include a heat and moisture exchanger (HME), a valve, a hands free valve, a shower guard or other known tracheostoma accessory which can be disposed in a housing that is engaged with the accessory mounting portion 18. Other retention features such as magnets, press fit, snap features or other known retention features can be used.

The central conical region 22 of the adjustable base plate 10 is formed with the flexible membrane 12 defining a plurality of web regions 34 between the conforming members 20. The conforming members 20 can resemble petals extending radially outwardly from the cylindrical accessory mounting portion 18. The conical region 22 defines a conical internal surface 22A and a conical external surface 22B with the accessory mounting portion 18 extending from the conical region 22. The thin film of the web regions 34 allow for the conical external surface of the conical region 22 to conform to different depths of tracheostomas as well as non-symmetrical geometries around the tracheostoma for creating a better seal than conventional flat base plate components. The conforming members 20 tend to remain adhered to the tracheostoma and adapt to the natural movement of the peristomal skin.

The plurality of conforming members 20 can include between three and fifteen conforming members that can be generally rectangular, triangular or trapezoidal in shape. In the example shown in FIG. 1, seven conforming members are shown. The web regions 32 between the conforming members can be generally triangular, rectangular or trapezoidal in shape. The conforming members 20 can all be similarly shaped and sized or can have differing shapes or sizes.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An adjustable base plate for use with a tracheostoma comprising:
   a flexible membrane having a first surface and a second surface;
   a base component bonded to the first surface of the flexible membrane and including an accessory mounting portion disposed in a center of the flexible membrane and adapted to mount a tracheostoma accessory, the base component further including between three and fifteen conforming members that extend radially outward directly from and are angled relative to the accessory mounting portion and are bonded to the first surface of the flexible membrane to define a conically shaped region with the between three and fifteen conforming members laterally spaced from one another, wherein the conforming members have a larger dimension in a lateral direction relative to a center axis of the accessory mounting portion than a thickness of the conforming members in a direction perpendicular to the center axis of the accessory mounting portion; and
   an adhesive material applied to the second surface of the flexible membrane for application to a user's skin while the between three and fifteen conforming members conform to natural movement of the user's skin.

2. An adjustable base plate for use with a tracheostoma comprising:
   a flexible membrane having a first surface and a second surface;
   a base component bonded to the first surface of the flexible membrane and including an accessory mounting portion disposed in a center of the flexible membrane and adapted to mount a tracheostoma accessory, the base component further including between three and fifteen conforming members that extend radially outward directly from and are angled relative to the accessory mounting portion and are bonded to the first surface of the flexible membrane to define a conically shaped region with the between three and fifteen conforming members laterally spaced from one another; and an adhesive material applied to the second surface of the flexible membrane for application to a user's skin while the between three and fifteen conforming members conform to natural movement of the user's skin;

wherein the conforming members are generally rectangular.

3. An adjustable base plate for use with a tracheostoma comprising:

a flexible membrane having a first surface and a second surface;

a base component bonded to the first surface of the flexible membrane and including an accessory mounting portion disposed in a center of the flexible membrane and adapted to mount a tracheostoma accessory, the base component further including between three and fifteen conforming members that extend radially outward directly from and are angled relative to the accessory mounting portion and are bonded to the first surface of the flexible membrane to define a conically shaped region with the between three and fifteen conforming members laterally spaced from one another; and an adhesive material applied to the second surface of the flexible membrane for application to a user's skin while the between three and fifteen conforming members conform to natural movement of the user's skin;

wherein the conforming members are generally trapezoidal.

4. The base plate according to claim 1, wherein the base component is made from one of polyurethane, ethylene vinyl acetate (EVA), polyvinyl chloride (PVC), silicone, or polyethylene.

5. The base plate according to claim 1, wherein the flexible, elastic membrane is made from one of polyurethane, ethylene vinyl acetate (EVA), polyvinyl chloride (PVC), silicone, or polyethylene.

6. The base plate according to claim 1, wherein the accessory mounting portion is generally cylindrical in shape.

7. The base plate according to claim 1, wherein the conically shaped region has an inner conical surface and an outer conical surface and the accessory mounting portion extends from the conically shaped region.

8. An adjustable base plate for use with a tracheostoma comprising:

a flexible membrane having a first surface and a second surface;

a base component bonded to the first surface of the flexible membrane and including an accessory mounting portion disposed in a center of the flexible membrane and adapted to mount a tracheostoma accessory, the base component further including between three and fifteen conforming members that extend radially outward directly from the accessory mounting portion and are bonded to the first surface of the flexible membrane with the between three and fifteen conforming members laterally spaced from one another, wherein the conforming members have a larger dimension in a lateral direction relative to a center axis of the accessory mounting portion than a thickness of the conforming members in a direction perpendicular to the center axis of the accessory mounting portion; and an adhesive material applied to the second surface of the flexible membrane for application to a user's skin while the between three and fifteen conforming members conform to natural movement of the user's skin.

9. An adjustable base plate for use with a tracheostoma comprising:

a flexible membrane having a first surface and a second surface;

a base component bonded to the first surface of the flexible membrane and including an accessory mounting portion disposed in a center of the flexible membrane and adapted to mount a tracheostoma accessory, the base component further including between three and fifteen conforming members that extend radially outward directly from the accessory mounting portion and are bonded to the first surface of the flexible membrane with the between three and fifteen conforming members laterally spaced from one another, wherein the conforming members have a larger dimension in a lateral direction relative to a center axis of the accessory mounting portion than a thickness of the conforming members in a direction perpendicular to the center axis of the accessory mounting portion; and an adhesive material applied to the second surface of the flexible membrane for application to a user's skin while the between three and fifteen conforming members conform to natural movement of the user's skin;

wherein the conforming members are generally rectangular.

10. An adjustable base plate for use with a tracheostoma comprising:

a flexible membrane having a first surface and a second surface;

a base component bonded to the first surface of the flexible membrane and including an accessory mounting portion disposed in a center of the flexible membrane and adapted to mount a tracheostoma accessory, the base component further including between three and fifteen conforming members that extend radially outward directly from the accessory mounting portion and are bonded to the first surface of the flexible membrane with the between three and fifteen conforming members laterally spaced from one another, wherein the conforming members have a larger dimension in a lateral direction relative to a center axis of the accessory mounting portion than a thickness of the conforming members in a direction perpendicular to the center axis of the accessory mounting portion; and an adhesive material applied to the second surface of the flexible membrane for application to a user's skin while the between three and fifteen conforming members conform to natural movement of the user's skin;

wherein the conforming members are generally trapezoidal.

11. The base plate according to claim 8, wherein the base component is made from one of polyurethane, ethylene vinyl acetate (EVA), polyvinyl chloride (PVC), silicone, or polyethylene.

12. The base plate according to claim 8, wherein the flexible membrane is made from one of polyurethane, ethylene vinyl acetate (EVA), polyvinyl chloride (PVC), silicone, or polyethylene.

13. The base plate according to claim 8, wherein the accessory mounting portion is generally cylindrical in shape.

14. The base plate according to claim 1, wherein the plurality of conforming members are bonded to the flexible membrane to form a conically shaped region that has an inner conical surface and an outer conical surface and the accessory mounting portion extends from the conically shaped region.

* * * * *